United States Patent
Clark et al.

(10) Patent No.: US 8,845,568 B2
(45) Date of Patent: Sep. 30, 2014

(54) DISTRACTOR STRAPS FOR USE WITH DISTRACTOR APPARATUSES

(75) Inventors: Andrew Clark, Arlington, MA (US); David Chella, Brighton, MA (US); Jesse Drake, Westborough, MA (US)

(73) Assignee: Allen Medical Systems, Inc., Batesville, IN (US)

( * ) Notice: Subject to any disclaimer, the term of this patent is extended or adjusted under 35 U.S.C. 154(b) by 218 days.

(21) Appl. No.: 13/435,040

(22) Filed: Mar. 30, 2012

(65) Prior Publication Data

US 2012/0259261 A1 Oct. 11, 2012

Related U.S. Application Data

(60) Provisional application No. 61/473,390, filed on Apr. 8, 211.

(51) Int. Cl.
*A61F 5/04* (2006.01)
*A61F 5/37* (2006.01)

(52) U.S. Cl.
CPC .................. *A61F 5/3776* (2013.01); *A61F 5/04* (2013.01)
USPC .............................................. 602/36; 602/32

(58) Field of Classification Search
CPC ........................................................ A61F 5/04
USPC ................ 602/32, 36, 4; 128/106.1, 876, 882
See application file for complete search history.

(56) References Cited

U.S. PATENT DOCUMENTS

| | | | |
|---|---|---|---|
| 2,198,908 A | 4/1940 | Ellis |
| 2,511,182 A | 6/1950 | Spencer |
| 2,644,448 A | 7/1953 | Jardine |
| 2,723,663 A | 11/1955 | Davis |
| 3,135,257 A | 6/1964 | Anderson |
| 3,385,292 A | 5/1968 | Hardy |
| 3,477,428 A | 11/1969 | Hare |
| 3,612,046 A | 10/1971 | Gaylord |
| 3,618,598 A | 11/1971 | Davis |
| 3,680,551 A | 8/1972 | Bell et al. |
| 3,680,552 A | 8/1972 | Bell et al. |
| 3,720,206 A | 3/1973 | Walker et al. |

(Continued)

FOREIGN PATENT DOCUMENTS

WO 01/45601 A2 6/2001

OTHER PUBLICATIONS

Innomed, Inc., "Shereff Ankle Distractor" and "Strap for Shereff Ankle Distractor", 2011.

(Continued)

*Primary Examiner* — Patricia Bianco
*Assistant Examiner* — Keri J Nelson
(74) *Attorney, Agent, or Firm* — Dinsmore & Shohl LLP

(57) ABSTRACT

Distractor straps for use with distractor apparatuses are disclosed. In one embodiment, a distractor strap includes a cinch strap having a free end and a second end. The second end of the cinch strap includes an adjustment mechanism receiving the free end of the cinch strap such that the cinch strap forms a closed loop. A diameter of the closed loop is adjustable with the adjustment mechanism. The distractor strap further includes a cross strap comprising a first loop, a second loop, and strapping connecting the first loop and the second loop. The cinch strap is positioned in the first loop and the second loop such that the cross strap extends across the diameter of the closed loop formed by the cinch strap and the cross strap and the cinch strap are slidable with respect to one another.

19 Claims, 11 Drawing Sheets

(56) References Cited

U.S. PATENT DOCUMENTS

| | | |
|---|---|---|
| 3,978,853 A | 9/1976 | Morrison |
| 4,144,880 A | 3/1979 | Daniels |
| 4,265,230 A | 5/1981 | Jordon |
| 4,350,153 A | 9/1982 | Borschneck |
| 4,443,005 A | 4/1984 | Sugarman et al. |
| 4,573,482 A | 3/1986 | Williams |
| 5,020,525 A | 6/1991 | Ewing et al. |
| 5,025,802 A | 6/1991 | Laico et al. |
| 5,027,799 A | 7/1991 | Laico et al. |
| 5,063,918 A | 11/1991 | Guhl |
| 5,100,129 A | 3/1992 | Porter et al. |
| 5,162,039 A | 11/1992 | Dahners |
| 5,290,220 A | 3/1994 | Guhl |
| 5,608,934 A | 3/1997 | Torrie et al. |
| 5,743,898 A | 4/1998 | Bailey et al. |
| 5,967,947 A | 10/1999 | Glover |
| 6,629,944 B2 | 10/2003 | Smart |
| 6,953,443 B2 | 10/2005 | Hay |
| 7,100,296 B2 | 9/2006 | Root |
| 7,131,955 B2 | 11/2006 | Price et al. |
| 7,243,654 B2 | 7/2007 | Schuerch |
| 7,244,238 B2 | 7/2007 | March et al. |
| 7,452,343 B2 | 11/2008 | Campbell |
| 7,641,624 B2 | 1/2010 | Kendrick |
| 7,771,378 B2 | 8/2010 | Price et al. |
| 7,832,401 B2 | 11/2010 | Torrie et al. |
| 7,857,780 B2 | 12/2010 | Sommers et al. |
| 7,947,006 B2 | 5/2011 | Torrie et al. |
| 7,947,862 B2 | 5/2011 | Livorsi |
| 2002/0128577 A1 | 9/2002 | Smart |
| 2004/0015114 A1 | 1/2004 | Hay |
| 2004/0133140 A1 | 7/2004 | Aduana, Jr. et al. |
| 2004/0167455 A1 | 8/2004 | Smart |
| 2006/0224096 A1 | 10/2006 | Lott |
| 2007/0265635 A1 | 11/2007 | Torrie et al. |
| 2007/0287946 A1 | 12/2007 | Kendrick |
| 2008/0103425 A1 | 5/2008 | Berlet |
| 2011/0190676 A1 | 8/2011 | Torrie et al. |

OTHER PUBLICATIONS

Smith & Nephew, Inc., "Acufex® Non-Invasive Ankle Distractor", Nov. 22, 1999.

Arthrocare Sports Medicine, "Ankle Distraction for Arthroscopic Surgery", 2007.

Extended European Search Report, Aug. 10, 2012, for EP application 12275036.

DISTRACTOR STRAPS FOR USE WITH DISTRACTOR APPARATUSES

CROSS REFERENCE TO RELATED APPLICATIONS

This application claims priority to U.S. Provisional Application Ser. No. 61/473,390 filed Apr. 8, 2011 and entitled "Distractor Straps For Use With Distractor Apparatuses," the entirety of which is incorporated herein by reference.

TECHNICAL FIELD

The present specification generally relates to apparatuses for limb distraction and, more specifically, to distractor straps for use in conjunction with distraction apparatuses for applying tension to a limb, such as a leg, during medical procedures.

BACKGROUND

Surgical procedures performed on a joint, such as an ankle, often require distraction or spreading of the joint to facilitate the insertion and manipulation of surgical implements in the joint. Conventional distractor apparatuses are attached to the limb in which the joint resides such that tension can be applied to the limb thereby spreading or decompressing the joint. The distractor apparatus may exert tension on the limb via a strap which is attached to both the distractor and the limb. For instance, where surgery is being performed on an ankle, the distractor apparatus is attached to a strap which is, in turn, attached to the foot and/or ankle. Tension may be applied to the leg and ankle with the distractor apparatus through the strap. Specifically, the tension is communicated to the limb through the strap thereby stretching the limb along its axis and expanding the joint.

Conventional strap designs have several drawbacks. For example, portions of the strap which extend around the heel of a patient may be formed to accommodate patients of various sizes. In these circumstances the distractor apparatus is utilized to take up excess slack in the distractor strap. However, because the strap contains excess material, a significant gap develops between the distal end of the limb and the distractor apparatus thereby hindering access to the joint of interest and increasing the difficulty of performing the surgical operation.

Accordingly, a need exists for alternative distractor straps which facilitate improved access to the extremities of a distracted limb.

SUMMARY

In one embodiment, a distractor strap for use with a distractor apparatus may include a cinch strap having a free end and a second end. The second end of the cinch strap may include an adjustment mechanism receiving the free end of the cinch strap such that the cinch strap forms a closed loop. A diameter of the closed loop may be adjustable with the adjustment mechanism. The distractor strap may also include a cross strap comprising a first loop, a second loop, and strapping connecting the first loop and the second loop. The cinch strap may be positioned in the first loop and the second loop such that the cross strap extends across the diameter of the closed loop formed by the cinch strap and the cross strap and the cinch strap are slidable with respect to one another.

In another embodiment, the distractor strap may include a cinch strap having a free end and a second end. The second end of the cinch strap may include an adjustment mechanism receiving the free end of the cinch strap such that the cinch strap forms a closed loop. A diameter of the closed loop may be adjustable with the adjustment mechanism. The distractor strap may also include a cinch pad attached to the cinch strap. The distractor strap may also include a cross strap comprising a first loop, a second loop, and strapping connecting the first loop and the second loop. The cross strap may further include a cross pad attached to at least the strapping. The cinch strap may be positioned in the first loop and the second loop of the cross strap such that the cross strap extends across the diameter of the closed loop formed by the cinch strap. The closed loop may have a front portion and a rear portion comprising the cinch pad with the cross strap positioned between the front portion and the rear portion. The adjustment mechanism may be coupled to the cinch strap at the front portion of the closed loop. The adjustment mechanism may include a ring for coupling the cinch strap to the distractor apparatus.

In yet another embodiment, a distractor strap for use with a distractor apparatus may include a cinch strap having a free end and a second. The second end of the cinch strap may include an adjustment mechanism receiving the free end of the cinch strap such that the cinch strap forms a closed loop. A diameter of the closed loop may be adjustable with the adjustment mechanism. The distractor strap may further include a cinch pad attached to the cinch strap such that the cinch pad is slidable on the cinch strap. The distractor strap may further include a cross strap comprising a first loop, a second loop, and strapping connecting the first loop and the second loop. The cross strap may further include a cross pad attached to at least the strapping. The cinch strap may be positioned in the first loop and the second loop such that the cross strap extends across the diameter of the closed loop formed by the cinch strap and the closed loop has a front portion and a rear portion comprising the cinch pad with the cross strap positioned between the front portion and the rear portion.

These and additional features provided by the embodiments described herein will be more fully understood in view of the following detailed description, in conjunction with the drawings.

BRIEF DESCRIPTION OF THE DRAWINGS

The embodiments set forth in the drawings are illustrative and exemplary in nature and not intended to limit the subject matter defined by the claims. The following detailed description of the illustrative embodiments can be understood when read in conjunction with the following drawings, where like structure is indicated with like reference numerals and in which:

DETAILED DESCRIPTION

Figure 1:
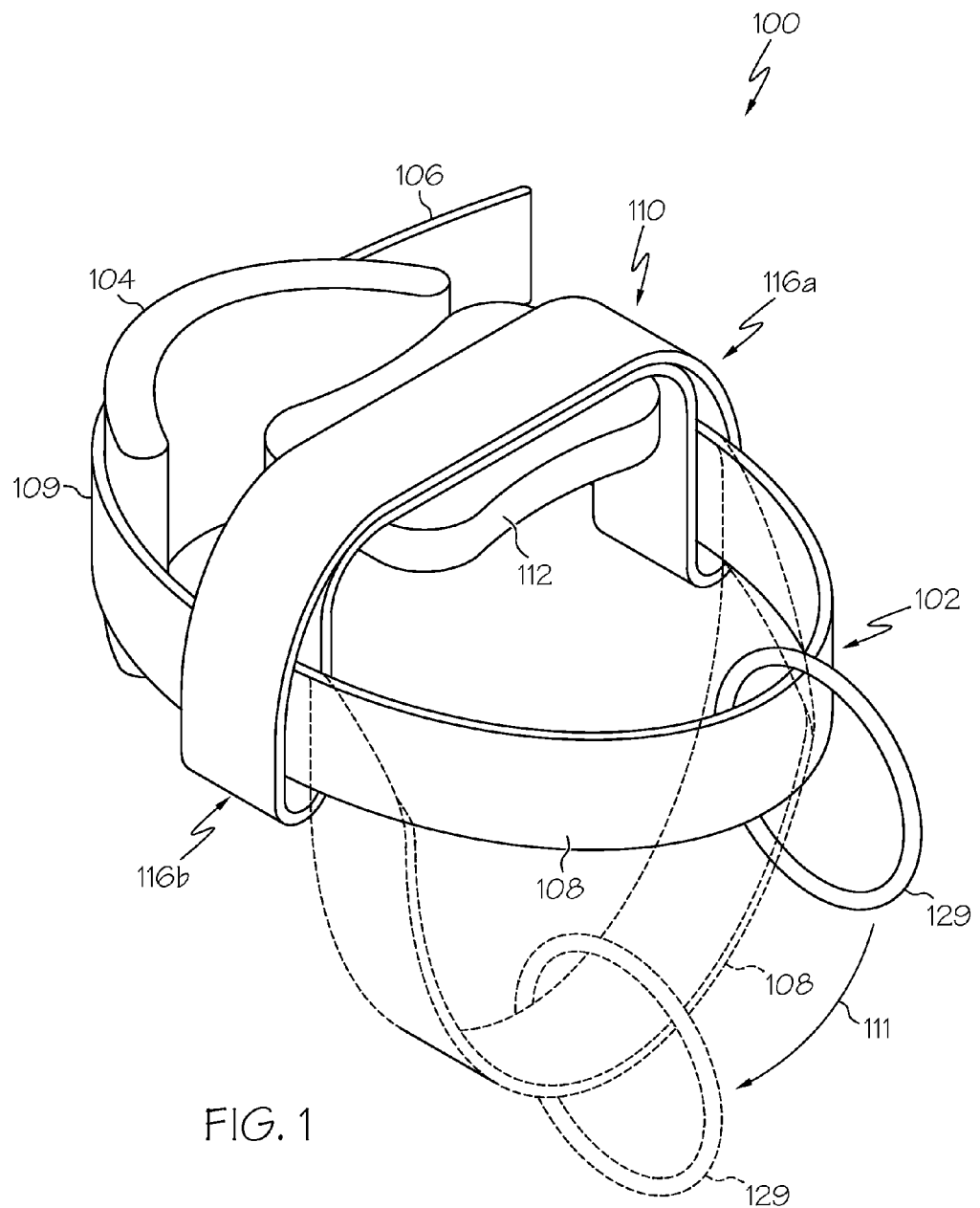
FIG. 1 is a front perspective view of a distractor strap according to one or more embodiments shown and described herein.

FIG. 1 generally depicts one embodiment of a distractor strap for use in applying tension to a limb of a patient, such as a leg, with a distractor apparatus. The distractor strap generally comprises a cinch strap with a cinch pad and a cross strap with a cross pad. A length or circumference of the cinch strap is adjustable to facilitate removing excess slack in the cinch strap thereby shortening the distance between the distal end of the limb and a distractor apparatus to which the distractor strap is attached. The distractor strap and methods for using the distractor strap will be described in more detail herein with specific reference to the appended drawings.

Referring now to FIGS. 1-4, a distractor strap 100 for use with a distractor apparatus is schematically depicted. As shown in FIG. 1, the distractor strap 100 generally comprises a cinch strap 102 and a cross strap 110. The cinch strap 102 is formed from a woven material, such as nylon or the like. The cinch strap 102 generally comprises a free end 106 and a second end 107 which is coupled to an adjustment mechanism 120. The free end is directed through the adjustment mechanism 120 such that the cinch strap 102 forms a closed loop, as depicted in FIGS. 1-4. A ring 129 may optionally be positioned on the cinch strap 102 to facilitate coupling the distractor strap to a distractor apparatus.

As shown in FIG. 1, the closed loop formed by the cinch strap 102 generally comprises a front portion 108 and a rear portion 109 with the cross strap 110 positioned between the front portion and the rear portion. The cinch strap 102 is sufficiently flexible such that the front portion 108 of the cinch strap 102 may be rotated downward (as indicated by arrow 111) with respect to the rear portion 109 of the cinch strap 102 such that the closed loop formed by the cinch strap 102 does not lie in a single plane. This facilitates simultaneously positioning a rear portion 109 of the cinch strap 102 behind the Achilles tendon while the front portion 108 is positioned beneath the sole of the foot, as will be described in more detail herein. Alternatively, the rear portion 109 of the cinch strap 102 may be positioned on the talus or top of the foot while the front portion is positioned behind the Achilles tendon.

Figure 2A:
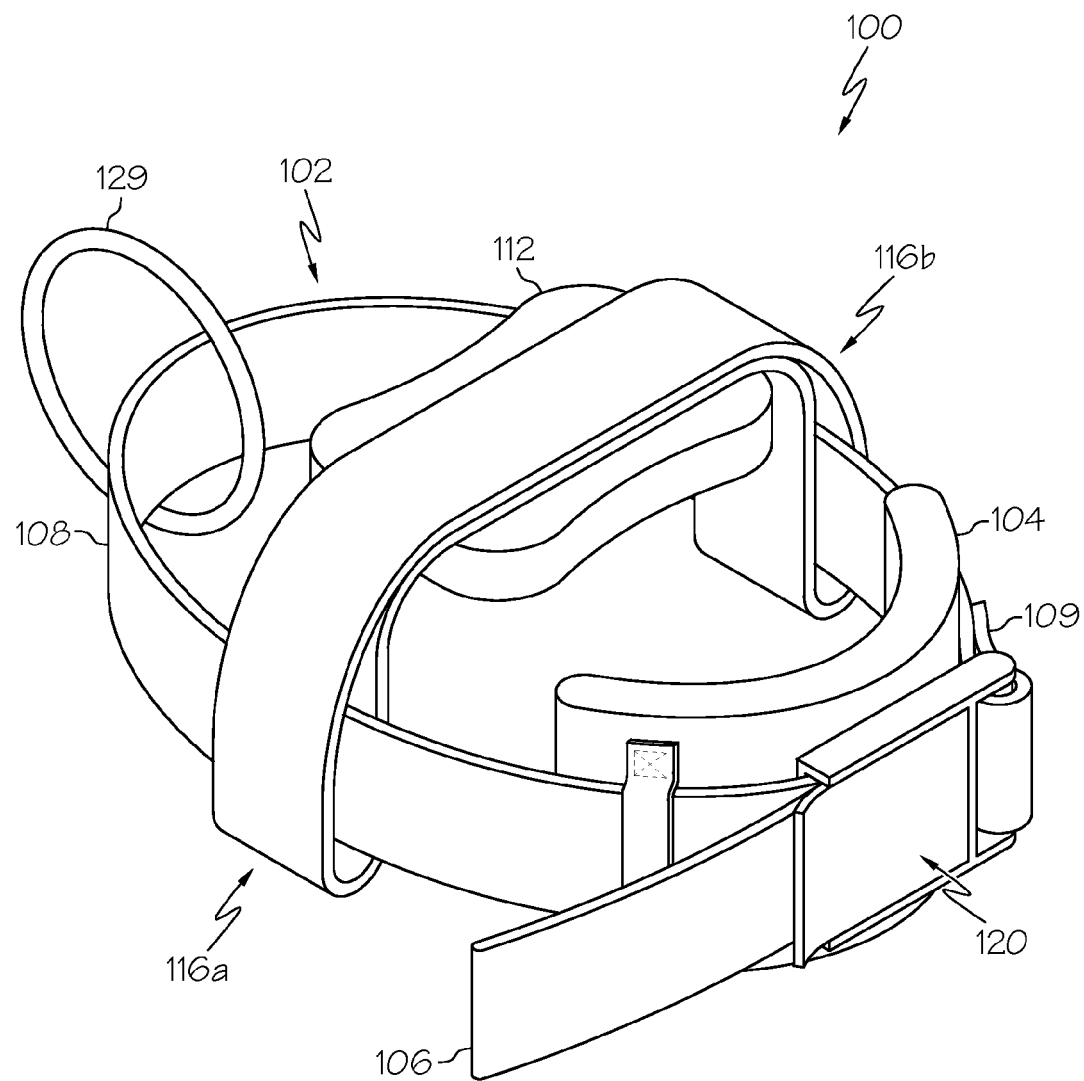
FIG. 2A is a rear perspective view of a distractor strap according to one or more embodiments shown and described herein.
Figure 2B:
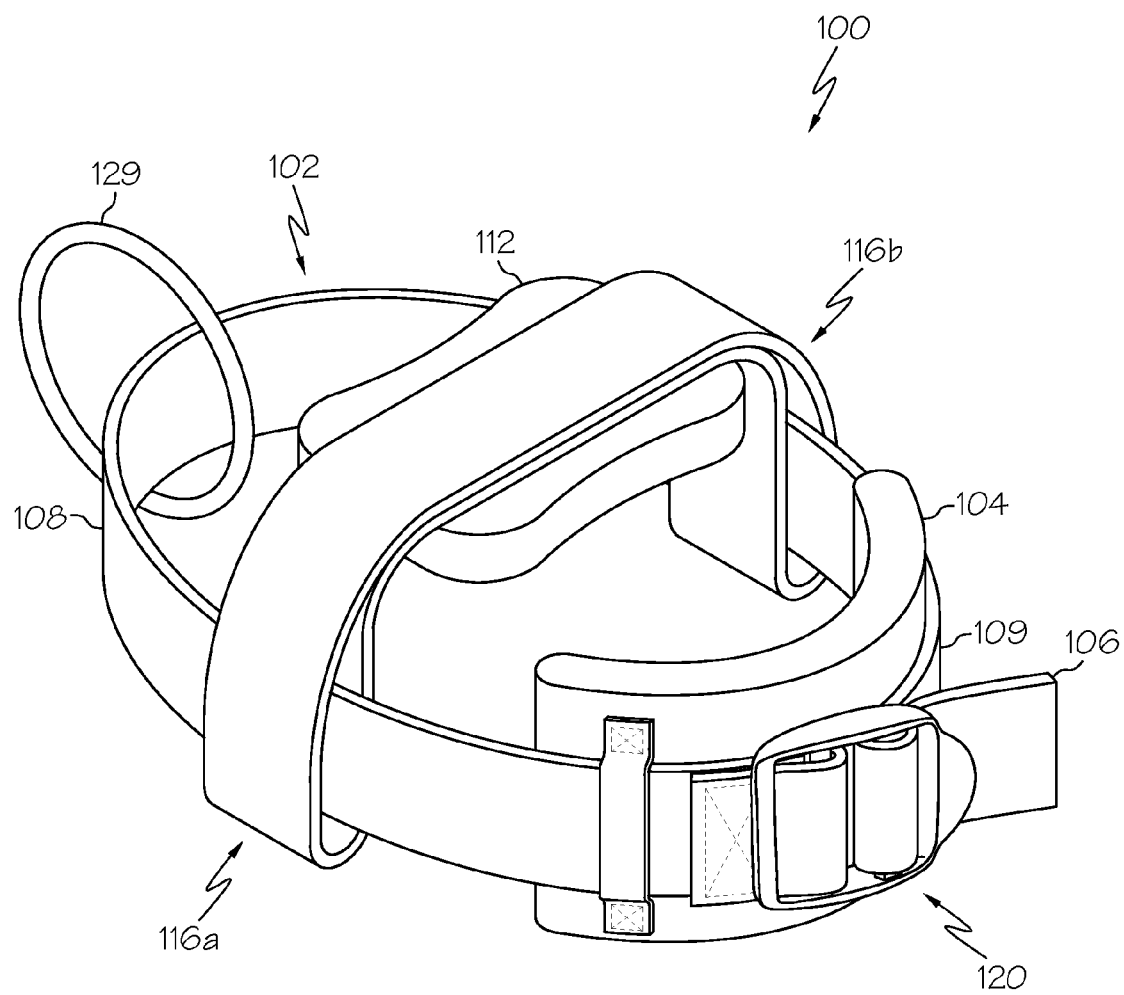
FIG. 2B is a rear perspective view of a distractor strap according to one or more embodiments shown and described herein.
Figure 2C:
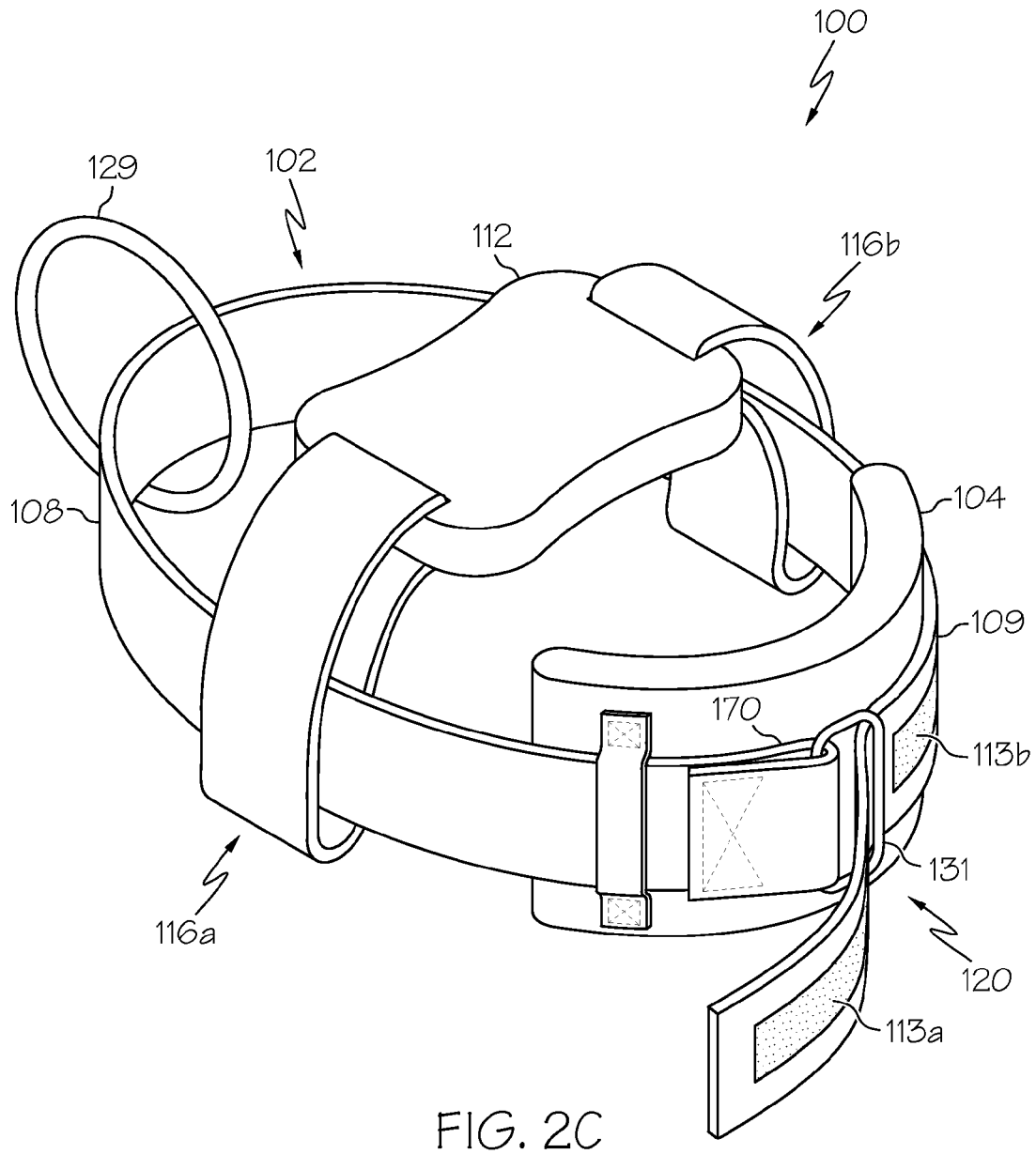
FIG. 2C is a rear perspective view of a distractor strap according to one or more embodiments shown and described herein.

Referring now to FIGS. 2A-2D the adjustment mechanism 120 facilitates adjusting the circumference of the cinch strap 102. For example, in the embodiment of the distractor strap 100 depicted in FIG. 2A, the adjustment mechanism 120 is a cam-lock buckle. Alternatively, the adjustment mechanism 120 may be a ladder-lock buckle, as schematically depicted in FIG. 2B. In yet another embodiment, the adjustment mechanism 120 may comprise a ring and a hook-and-loop fastener, as depicted in FIG. 2C. For example, in this embodiment, the second end 107 of the cinch strap 102 may be coupled to a ring 131, such as a square ring or a D-ring, and the free end 106 of the cinch strap may comprises a hook-and-loop fastener system 113a, 113b. The free end 106 of the cinch strap 102 may be directed through the ring 131 and folded back on itself to engage "hook" portions of the fastener system with the "loop" portions of the fastener system thereby securing the cinch strap to itself. In each of these embodiments, the circumference of the closed loop may be adjusted with the adjustment mechanism 120 to accommodate patients of different sizes and to remove excess slack from the cinch strap 102 of the distractor strap 100.

In the embodiments of the distractor strap 100 depicted in FIGS. 2A-2C, the adjustment mechanism 120 of the distractor strap 100 is positioned proximate a cinch pad 104 of the distractor strap. However, it should be understood that this is one exemplary relative orientation of the adjustment mechanism 120 and the cinch pad 104 of the distractor strap 100. In other embodiments, the adjustment mechanism 120 may be spaced apart or offset from the cinch pad 104 about the circumference of the cinch strap 102, such as when the adjustment mechanism 120 is located on a side of the cinch strap 102.

Figure 2D:
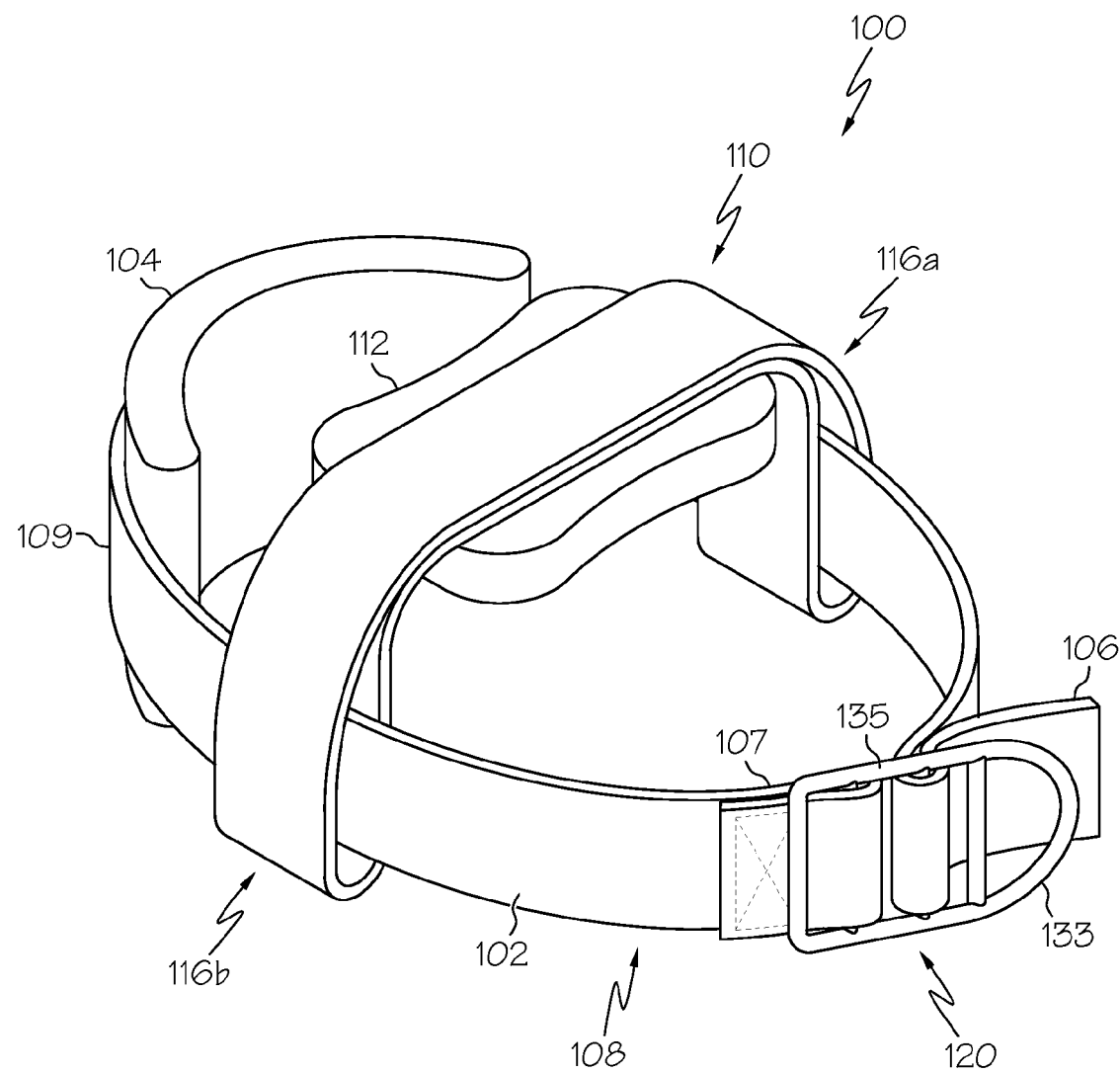
FIG. 2D is a front perspective view of the distractor strap according to one or more embodiments shown and described herein.

Referring to FIG. 2D, by way of example, in one embodiment, the cinch pad 104 of the distractor strap 100 is positioned in the rear portion 109 of the closed loop formed by the cinch strap 102. In this embodiment, the adjustment mechanism 120 is coupled to the front portion 108 of the cinch strap 102. Specifically, the adjustment mechanism 120 is coupled to the second end 107 of the cinch strap 102 while a free end 106 of the cinch strap is directed through the adjustment mechanism 120 such that a circumference of the closed loop formed by the cinch strap 102 is adjustable. In the embodiment shown in FIG. 2D, the adjustment mechanism 120 includes a ladder lock buckle portion 135 and a ring portion 133. In this embodiment, the ladder lock buckle portion 135 and the ring portion 133 are integrally formed with one another. However, in other embodiments, the ladder lock buckle portion 135 and the ring portion 133 may be separately formed and later joined, such as with adhesive, fasteners or the like. In this embodiment, the ladder lock buckle portion 135 facilitates adjusting the cinch strap 102 and the ring portion 133 facilitates coupling the front portion 108 of the closed loop to a distractor apparatus.

Figure 3:
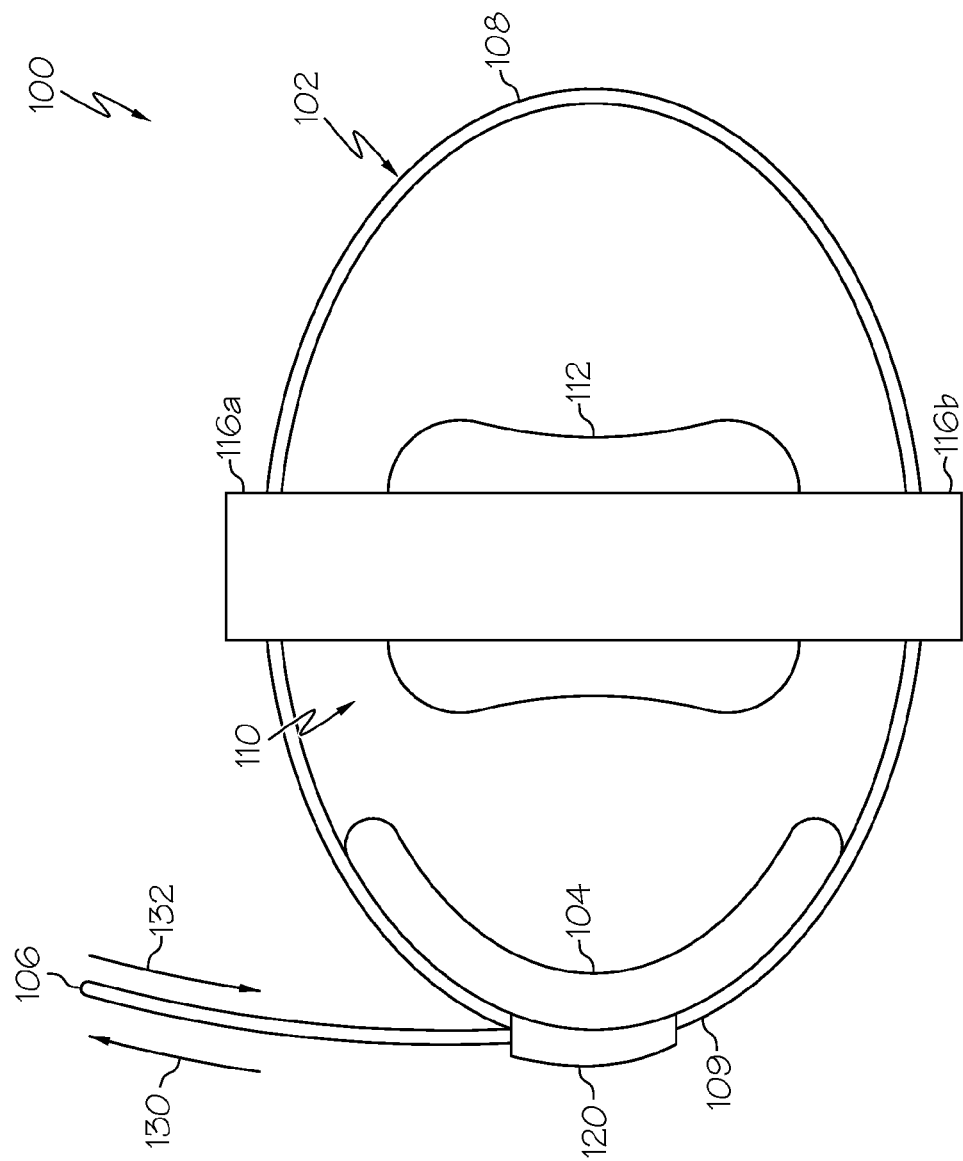
FIG. 3 is a top perspective view of the distractor strap of FIG. 1.
Figure 4:
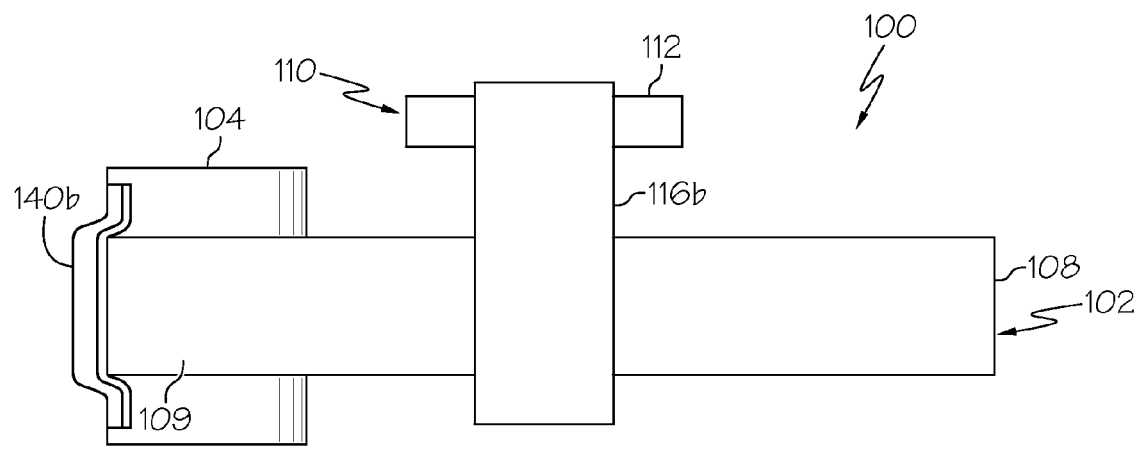
FIG. 4 is a side perspective view of the distractor strap of FIG. 1.
Figure 5:
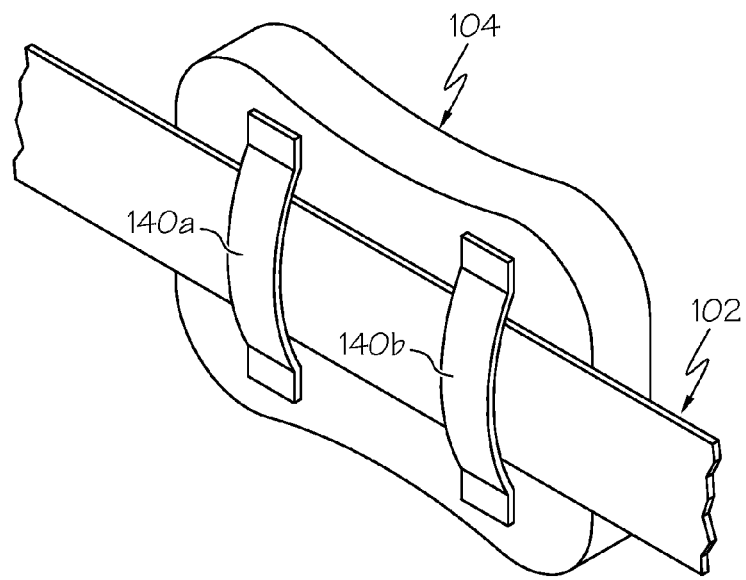
FIG. 5 schematically depicts a cinch pad for a distractor strap according to one or more embodiments shown and described herein.
Figure 6:
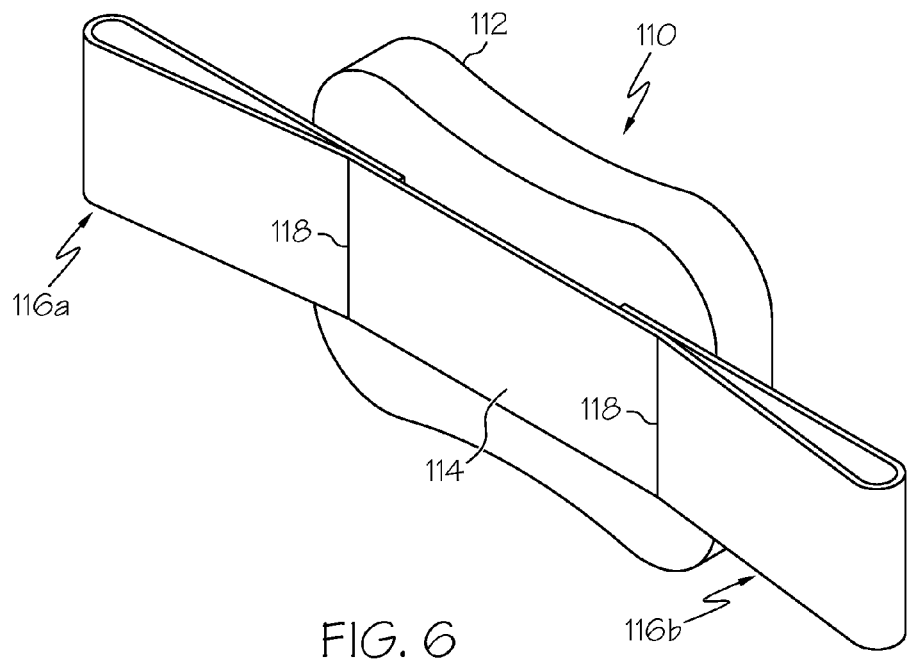
FIG. 6 schematically depicts a cross pad for a distractor strap according to one or more embodiments shown and described herein.
Figure 7:
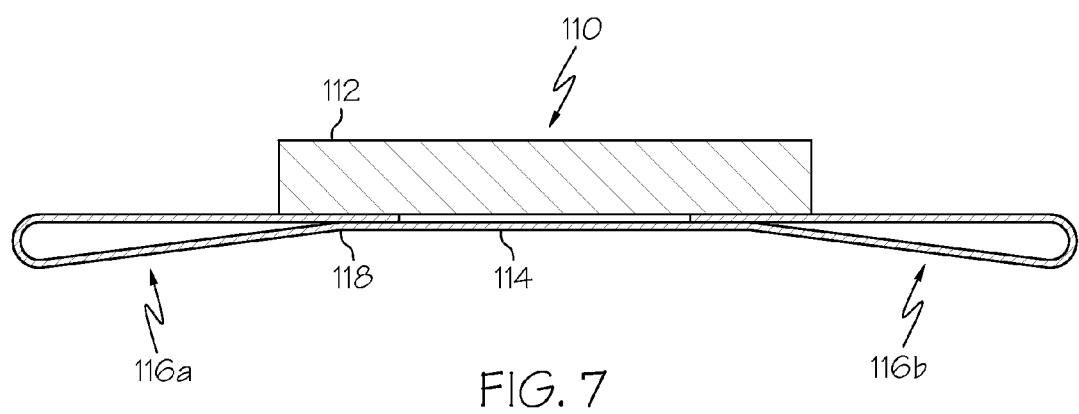
FIG. 7 schematically depicts a side view of the cross pad of FIG. 6.

Referring now to FIG. 3, an embodiment of the distractor strap 100 is depicted in which the adjustment mechanism 120 is a cam-lock buckle, as described above. The circumference of the closed loop formed by the cinch strap 102 can be adjusted by loosening the cam-lock buckle such that the cinch strap 102 is able to slide through the buckle. The circumference of the closed loop formed by the cinch strap can be increased by directing the cinch strap 102 through the adjustment mechanism in a loosening direction as indicated by arrow 132. The circumference of the closed loop formed by the cinch strap 102 can be decreased by directing the cinch strap 102 through the adjustment mechanism in a tightening direction as indicated by arrow 130.

Referring now to FIGS. 1 and 3-5, the cinch strap 102 may further comprise a cinch pad 104. The cinch pad 104 may be formed from cushioning material, such as a urethane foam, or another suitable cushioning material. The cinch pad 104 is generally positioned on the rear portion 109 of the cinch strap 102 to apply cushioning to the Achilles tendon when the distractor strap 100 is attached to the lower leg of a patient.

In one embodiment, the cinch pad 104 is affixed to the cinch strap 102. In this embodiment, the cinch pad 104 may be adhesively bonded to the cinch strap 102 or, alternatively, the cinch pad 104 may be stitched to the cinch strap 102 such that the cinch pad is not adjustable relative to the cinch strap 102.

In another embodiment, the cinch pad 104 is adjustable on the cinch strap 102. For example, referring to FIG. 5, the cinch pad 104 may include a pair of pad loops 140a, 140b which are attached to the cinch pad with adhesive and/or stitching. The cinch strap 102 may pass between the pad loops 140a, 140b and the cinch pad 104 such that the cinch pad 104 is slidable with respect to the cinch strap 102 which facilitates adjusting the cinch pad 104 on the cinch strap 102. This allows the cinch pad 104 to be positioned and repositioned one the cinch strap 102 as the circumference of the closed loop formed by the cinch strap 102 is increased or decreased.

While the cinch pad 104 has been described herein as adjustable with respect to the cinch strap 102, it should be understood that, in alternative embodiments, the cinch pad 104 may be fixed to the cinch strap 102. For example, the cinch pad 104 may be fixedly attached to the cinch strap 102 proximate the second end of the cinch strap 102.

Referring now to FIGS. 1, 3 and 6-7, the distractor strap 100 further comprises a cross strap 110. The cross strap 110 generally comprises strapping 114 formed from a flexible material such as, for example, nylon. The strapping 114 extends between two strap loops 116a, 116b which facilitate slidably coupling the cross strap 110 to the cinch strap 102. In the embodiments described herein, the strapping 114 and strap loops 116a, 116b are formed from a single length of material by folding the ends of the material back on itself and securing the ends by stitching 118 and/or adhesive.

The cross strap 110 optionally comprises a cross pad 112. The cross pad 112 is formed from a cushioning material such as urethane foam rubber or a similar cushioning material. In the embodiments described herein the cross pad 112 is attached to at least the strapping 114 with stitching 118 and/or adhesive.

As described hereinabove, the cross strap 110 is slidably coupled to the cinch strap 102. Specifically, the cinch strap 102 is directed through the strap loops 116a, 116b such that the cross strap 110 extends across the diameter of the closed loop formed by the cinch strap 102 (see e.g., FIGS. 1 and 3) when the free end 106 of the cinch strap 102 is directed through the adjustment mechanism 120. Accordingly, it should be understood that the position of the cross strap 110 on the cinch strap 102 is adjustable.

Figure 9:
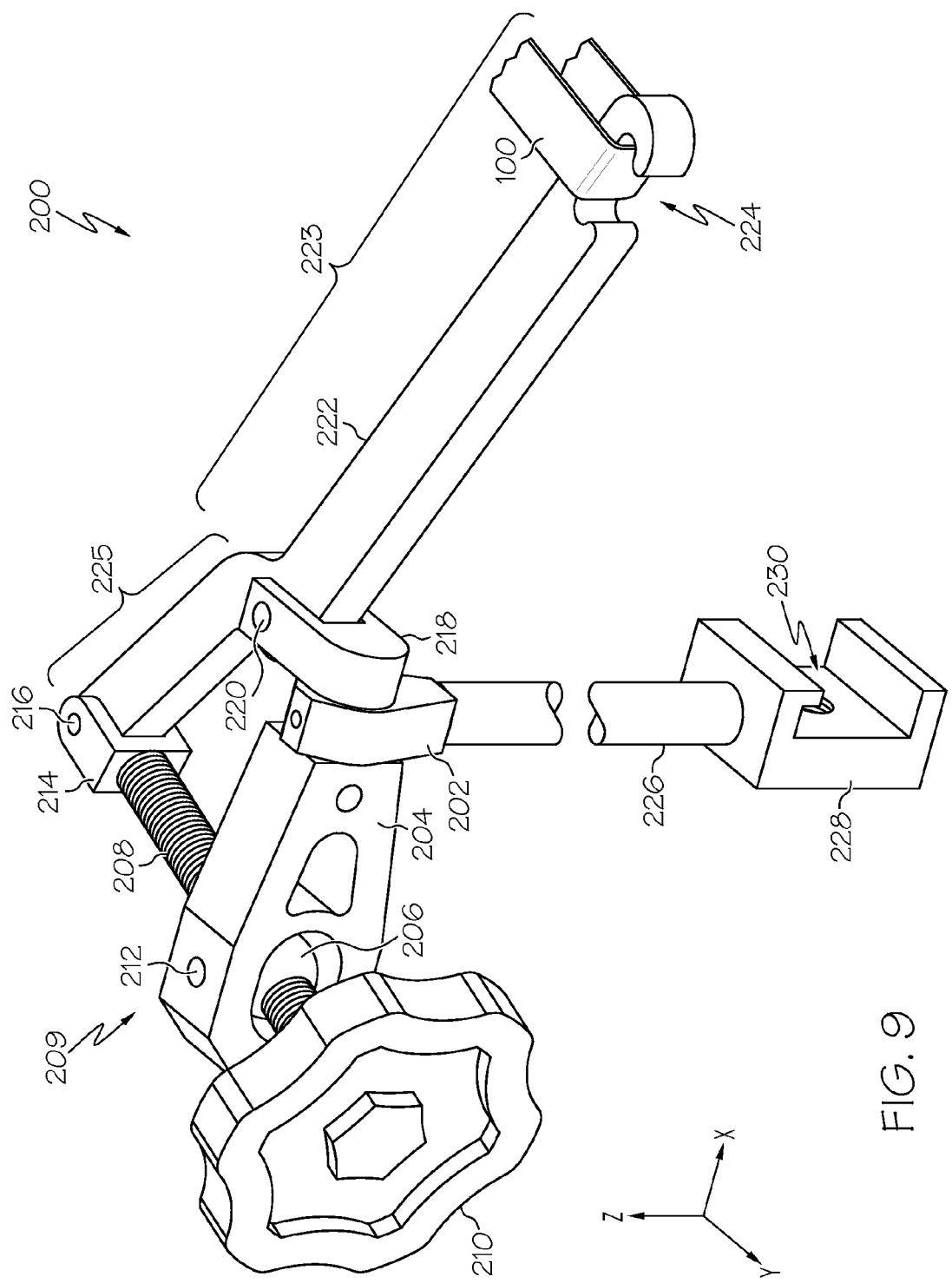
FIG. 9 schematically depicts one embodiment of a distractor apparatus for use with a distractor strap.

The embodiments of the distractor strap 100 described herein may be used in conjunction with a distractor apparatus to apply a distraction force to the lower leg. An exemplary distractor apparatus 200 is schematically depicted in FIG. 9. However, it should be understood that the embodiments of the distractor strap 100 described herein may be used with distractor apparatuses of various designs other than that depicted in FIG. 9.

Referring now to FIG. 9, a distractor apparatus 200 is schematically depicted. The distractor apparatus 200 generally comprises a mounting body 202, a frame 204, a tensioning mechanism 209 and a distractor arm 222. The mounting body 202 is disposed on a first end of a support 226 which, in the embodiment shown in FIG. 9, is constructed as a cylindrical rod. The second end of the support 226 is coupled to a connector 228 with a slot 230 to facilitate coupling the distractor apparatus 200 to an accessory rail (not shown) attached to a piece of medical equipment (not shown) such as, for example, a hospital bed or operating table.

The frame 204 and a body yoke 218 are rotatably coupled to the mounting body 202 with an axle (not shown) which extends from the frame 204, through the mounting body 202 and into the body yoke 218. In one embodiment (not shown), the axle is integrally formed with at least one of the frame 204 or the body yoke 218. In another embodiment, the axle is a separate component which is positioned in bores (not shown) formed in the frame 204 and the body yoke 218 and secured with set screws. The mounting body 202 may further comprise one or more bearings (not shown) through which the axle extends to facilitate rotation of the frame 204 and body yoke 218 relative to the mounting body 202.

The frame 204 extends from the mounting body 202 such that the frame is generally at a right angle with respect to the support 226. The frame 204 is formed with at least one opening in which a pivot nut 206 is positioned. Specifically, the pivot nut 206 is disposed in the frame 204 and secured with pivot pins 212 (one shown in FIG. 9) such that the pivot nut 206 is free to rotate with respect to the frame 204 while being secured to the frame 204.

The tensioning mechanism 209 generally comprises a threaded rod 208, a control knob 210 and a rod yoke 214. The threaded rod 208 is threaded through the pivot nut 206 of the frame 204 such that a portion of the threaded rod 208 extends from either side of the frame. The control knob 210 is secured to a first end of the threaded rod 208 and the rod yoke 214 is secured to the second end of the threaded rod 208.

The distractor arm 222 is an elongated lever comprising a first portion 223 and a second portion 225. In the embodiments described herein, the first portion 223 of the distractor arm 222 is generally longer than the second portion 225 of the distractor arm 222 to increase the range of travel and the torque applied to the receiving hook 224 with the tensioning mechanism 209. The distractor arm 222 includes a receiving hook 224 at the free end of the first portion 223 to facilitate attaching one or more accessories, such as a tensioning strap, tension gauge, or the like, to the distractor arm 222. The distractor arm 222 is pivotally coupled to the rod yoke 214 and the body yoke 218 such that the receiving hook 224 is pivotable with respect to the mounting body 202. Specifically, the body yoke 219 is coupled to the distractor arm 222 with pivot pin 220 such that the distractor arm 222 is pivotable about the pivot pin 220. Similarly, the rod yoke 214 is coupled to the second portion 225 of the distractor arm 222 with pivot pin 216. In the embodiments shown herein, the first portion 223 of the distractor arm 222 transitions into the second portion 225 of the distractor arm 222 proximate the pivot pin 220 coupling the distractor arm 222 to the body yoke 218. In the embodiment of the distractor apparatus 200 depicted in FIG. 9 the distractor arm 222 is coupled to the body yoke 218 and the rod yoke 214 such that the distractor arm 222 is substantially horizontally oriented (i.e., the distractor arm is within +/− degrees from parallel with the x-y plane of the coordinate axes of FIG. 9). Accordingly, it should be understood that the distractor arm 222 is pivotable with respect to the mounting body 202 in the x-y plane of the coordinate axes of FIG. 9.

Still referring to FIG. 9, a distracting force may be applied to a distractor strap 100 (partially depicted in FIG. 9) attached to the receiving hook by actuating the tensioning mechanism 209 with control knob 210. Specifically, rotating the control knob 210 in a tensioning direction (which is the clockwise direction in this example) causes the threaded rod 208 to rotate in the pivot nut thereby advancing the threaded rod 208 towards the distractor arm 222. As the threaded rod 208 advances it exerts a force on the distractor arm 222 through the rod yoke 214. The force applied to the distractor arm 222 causes the distractor arm 222 to rotate in a clockwise direction in the body yoke 218 about the pivot pin 220 which, in turn, causes the receiving hook 224 of the distractor arm 222 to advance in the clockwise direction such that a distraction force may be applied to the distractor strap 100 and to a limb attached to the strap.

Figure 8A:
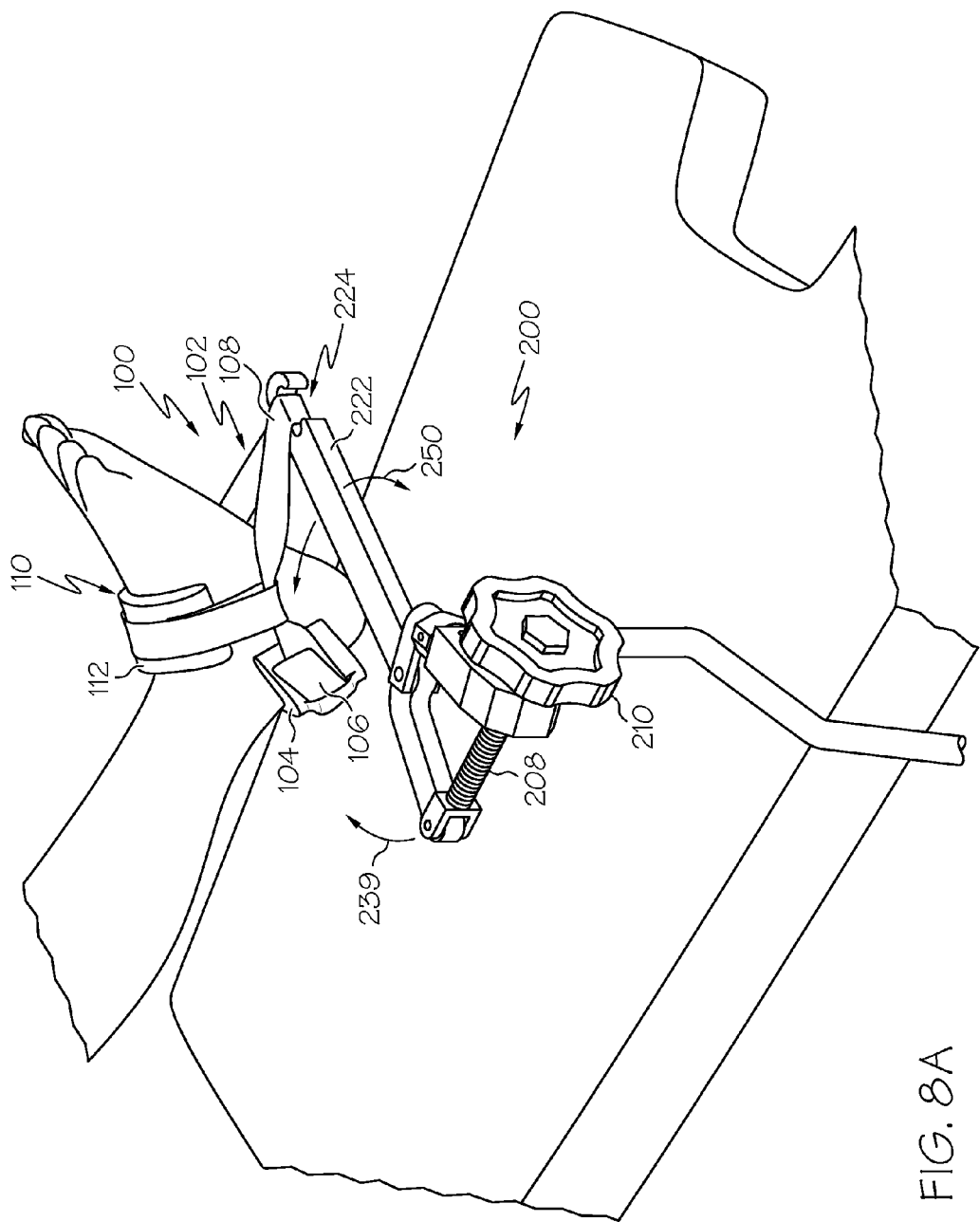
FIG. 8A schematically depicts a distractor strap being used in conjunction with a distractor apparatus to apply a distraction force to the lower leg of a patient according to one embodiment described herein.

Referring to FIG. 8A, a distractor strap 100 is shown in use with a distractor apparatus 200 to apply a distraction force to the lower leg of a patient. The distractor strap 100 is first positioned on the ankle such that the cinch pad 104 is located on the Achilles tendon to provide cushioning. The front portion 108 of the cinch strap 102 is then positioned under the sole of the foot, as depicted in FIG. 8. The length (i.e., the circumference) of the cinch strap 102 is then decreased by loosening the adjustment mechanism (not shown in FIG. 8) and applying a tension to the free end 106 of the cinch strap 102. This decreases the circumference of the cinch strap 102 thereby taking up slack in the cinch strap 102 and drawing the front portion 108 of the cinch strap 102 closer to the sole of the foot. Once the length of the cinch strap 102 has been adjusted, the position of the cross strap 110 is adjusted on the cinch strap 102 such that the cross pad 112 is generally positioned over the talus and/or the tarsals of the foot.

Once the distractor strap 100 is positioned on the ankle and foot, the front portion 108 of the cinch strap 102 is coupled to the receiving hook 224 of the distractor arm 222 of the distractor apparatus 200. For example, in the embodiment shown in FIG. 8, the distractor arm 222 is inserted through the cinch strap 102 such that a front portion 108 of the cinch strap 102 is received in the receiving hook 224. In other embodiments (not shown) one or more rings, such as D-rings or the like as described above, may be attached to the cinch strap 102 and/or the receiving hook to facilitate connecting the distractor strap 100 to the distractor arm 222 of the distractor apparatus 200.

Figure 8B:
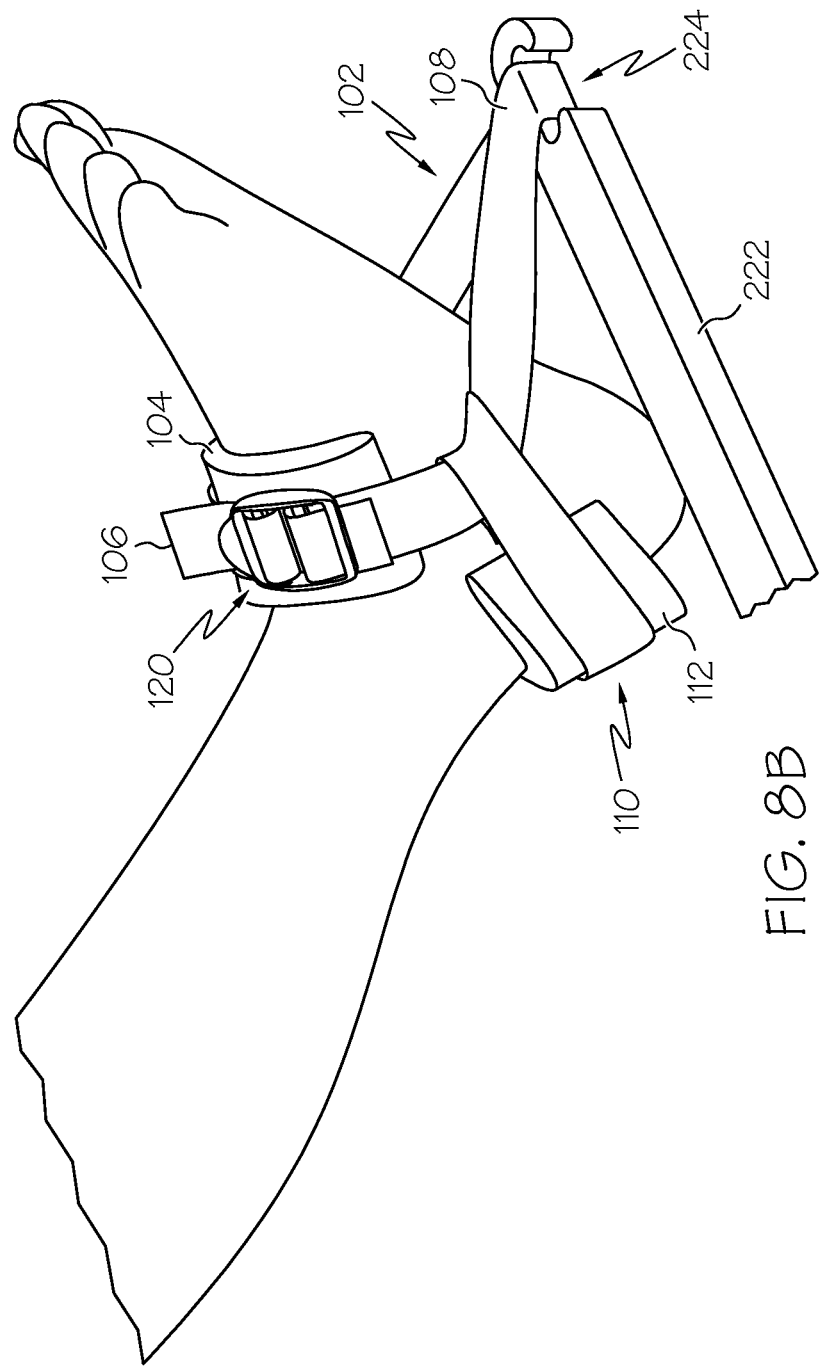
FIG. 8B schematically depicts a distractor strap being used in conjunction with a distractor apparatus to apply a distraction force to the lower leg of a patient according to one embodiment described herein.

Referring to FIG. 8B, in the alternative, the distractor strap may be positioned on the lower leg of the patient such that the cinch pad is positioned on the talus and the cross pad is positioned behind the Achilles tendon. In this embodiment, the distractor strap 100 is first positioned on the ankle such that the cinch pad 104 is located on the talus or top of the foot to provide cushioning. The front portion 108 of the cinch strap 102 is then positioned under the sole of the foot, as depicted in FIG. 8B. The cross strap 110 is adjusted on the cinch strap 102 such that the cross pad 112 is generally positioned behind the Achilles tendon of the patient. The length (i.e., the circumference) of the cinch strap 102 is then decreased by applying a tension to the free end 106 of the cinch strap 102. This decreases the circumference of the cinch strap 102 thereby taking up slack in the cinch strap 102 and drawing the front portion 108 of the cinch strap 102 closer to the sole of the foot.

Once the distractor strap 100 is positioned on the ankle and foot, the front portion 108 of the cinch strap 102 is coupled to the receiving hook 224 of the distractor arm 222 of the distractor apparatus 200. For example, in the embodiment shown in FIG. 8B, the distractor arm 222 is inserted through the cinch strap 102 such that a front portion 108 of the cinch strap 102 is received in the receiving hook 224. In other embodiments (not shown) one or more rings, such as D-rings or the like as described above, may be attached to the cinch strap 102 and/or the receiving hook to facilitate connecting the distractor strap 100 to the distractor arm 222 of the distractor apparatus 200.

Once the distractor strap 100 is attached to the distractor arm 222, the control knob 210 is rotated in a direction which advances the threaded rod 208 in the direction indicated by arrow 239. As the threaded rod 208 is advanced, the distractor arm 222 is rotated in the direction indicated by arrow 250 (i.e., clockwise) such that tension is applied to the distractor strap 100 and, in turn, the lower leg, thereby distracting the ankle joint.

It should now be understood that the embodiments described herein generally relate to distractor straps for use in conjunction with distractor apparatuses. The distractor straps may be used to apply a distraction force to a limb, such as the leg, such that a surgical procedure may be formed within a joint. The embodiments of the distractor straps described herein facilitate adjusting the length or circumference of the cinch strap of the distractor strap to accommodate patients of different sizes and to eliminate excess slack in the distractor strap. Eliminating the excess slack in the distractor strap reduced the distance between the distractor apparatus and the distal end of the limb thereby improving access to the distal end of the limb.

It is noted that the terms "substantially" and "about" may be utilized herein to represent the inherent degree of uncertainty that may be attributed to any quantitative comparison, value, measurement, or other representation. These terms are also utilized herein to represent the degree by which a quantitative representation may vary from a stated reference without resulting in a change in the basic function of the subject matter at issue.

While particular embodiments have been illustrated and described herein, it should be understood that various other changes and modifications may be made without departing from the spirit and scope of the claimed subject matter. Moreover, although various aspects of the claimed subject matter have been described herein, such aspects need not be utilized in combination. It is therefore intended that the appended claims cover all such changes and modifications that are within the scope of the claimed subject matter.

What is claimed is:

1. A distractor strap for use with a distractor apparatus, the distractor strap comprising:
a cinch strap having a free end and a second end, the second end of the cinch strap comprising an adjustment mechanism receiving the free end of the cinch strap such that the cinch strap forms a closed loop, wherein a diameter of the closed loop is adjustable with the adjustment mechanism; and
a cross strap comprising a first loop, a second loop, and strapping connecting the first loop and the second loop, wherein the cinch strap is positioned in the first loop and the second loop such that the cross strap extends across the diameter of the closed loop formed by the cinch strap and the cross strap and the cinch strap are slidable with respect to one another when the cross strap is secured to the cinch strap
wherein the cross strap further comprises a cross pad attached to at least the strapping.

2. The distractor strap of claim 1, wherein the adjustment mechanism is a cam lock buckle coupled to the second end of the cinch strap.

3. The distractor strap of claim 1, wherein the adjustment mechanism is a ladder lock buckle coupled to the second end of the cinch strap.

4. The distractor strap of claim 3, wherein the ladder lock buckle comprises a ring for coupling the distractor strap to the distractor apparatus.

5. The distractor strap of claim 4, wherein the ladder lock buckle is integrally formed with the ring.

6. The distractor strap of claim 1, wherein the adjustment mechanism comprises a hook-and-loop closure coupled to the cinch strap proximate the free end and a ring coupled to the second end of the cinch strap.

7. The distractor strap of claim 1, further comprising a cinch pad attached to the cinch strap.

8. The distractor strap of claim 7, wherein the cinch pad is slidable with respect to the cinch strap.

9. The distractor strap of claim 7, wherein the cinch pad comprises a pair of pad loops and the cinch strap is directed through the pair of pad loops such that the cinch pad is slidable on the cinch strap.

10. The distractor strap of claim 7, wherein:
the closed loop formed by the cinch strap has a front portion and a rear portion comprising the cinch pad, wherein the cross strap is positioned between the front portion and the rear portion;
the adjustment mechanism is coupled to the cinch strap at the front portion of the closed loop; and
the adjustment mechanism is a ladder lock buckle integrally formed with a ring for coupling the distractor strap to the distractor apparatus.

11. The distractor strap of claim 7, wherein the adjustment mechanism is offset from the cinch pad about a circumference of the closed loop formed by the cinch strap.

12. The distractor strap of claim 7, wherein the cinch pad is attached to the cinch strap at the second end of the cinch strap.

13. The distractor strap of claim 1, wherein the cross pad is fixedly attached to the cross strap.

14. The distractor strap of claim 1, further comprising a ring positioned on the cinch strap for coupling the distractor strap to the distractor apparatus.

15. The distractor strap of claim 1, wherein the adjustment mechanism comprises a ring for coupling the distractor strap to the distractor apparatus.

16. A distractor strap for use with a distractor apparatus, the distractor strap comprising:
a cinch strap having a free end and a second end, the second end of the cinch strap comprising an adjustment mechanism receiving the free end of the cinch strap such that the cinch strap forms a closed loop, wherein a diameter of the closed loop is adjustable with the adjustment mechanism;
a cinch pad attached to the cinch strap; and
a cross strap comprising a first loop, a second loop, strapping connecting the first loop and the second loop, and a cross pad attached to at least the strapping, wherein:
the cinch strap is positioned in the first loop and the second loop such that the cross strap extends across the diameter of the closed loop formed by the cinch strap and the closed loop has a front portion and a rear portion comprising the cinch pad with the cross strap positioned between the front portion and the rear portion; and
the cross strap and the cinch strap are slidable with respect to one another when the cross strap is secured to the cinch strap.

17. The distractor strap of claim 16, wherein the adjustment mechanism is a ladder lock buckle integrally formed with a ring for coupling the cinch strap to the distractor apparatus.

18. The distractor strap of claim 16, wherein:
the adjustment mechanism is coupled to the cinch strap at the front portion of the closed loop; and
the adjustment mechanism is a ladder lock buckle integrally formed with a ring for coupling the cinch strap to the distractor apparatus.

19. A distractor strap for use with a distractor apparatus, the distractor strap comprising:
a cinch strap having a free end and a second end, the second end of the cinch strap comprising an adjustment mechanism receiving the free end of the cinch strap such that the cinch strap forms a closed loop, wherein a diameter of the closed loop is adjustable with the adjustment mechanism;
a cinch pad attached to the cinch strap such that the cinch pad is slidable on the cinch strap; and
a cross strap comprising a first loop, a second loop, strapping connecting the first loop and the second loop, and a cross pad attached to at least the strapping, wherein the cinch strap is positioned in the first loop and the second loop such that the cross strap extends across the diameter of the closed loop formed by the cinch strap, the closed loop has a front portion and a rear portion comprising the cinch pad with the cross strap positioned between the front portion and the rear portion, and the cross strap and the cinch strap are slidable with respect to one another when the cross strap is secured to the cinch strap, wherein the adjustment mechanism is coupled to the cinch strap at the front portion of the closed loop, the adjustment mechanism comprising a ring for coupling the cinch strap to the distractor apparatus.

* * * * *